(12) United States Patent
Cross et al.

(10) Patent No.: US 8,133,729 B2
(45) Date of Patent: Mar. 13, 2012

(54) BIOMIMETIC UROTHELIUM

(75) Inventors: William Richard Cross, York (GB); Jennifer Southgate, York (GB)

(73) Assignee: The University of York, York (GB)

( * ) Notice: Subject to any disclaimer, the term of this patent is extended or adjusted under 35 U.S.C. 154(b) by 0 days.

(21) Appl. No.: 10/522,371

(22) PCT Filed: Jul. 28, 2003

(86) PCT No.: PCT/GB03/03291
§ 371 (c)(1),
(2), (4) Date: Jan. 25, 2005

(87) PCT Pub. No.: WO2004/011630
PCT Pub. Date: Feb. 5, 2004

(65) Prior Publication Data
US 2005/0233445 A1      Oct. 20, 2005

(30) Foreign Application Priority Data

Jul. 26, 2002    (GB) ................................. 0217314.4

(51) Int. Cl.
*C12N 5/00*      (2006.01)
*C12N 5/071*     (2010.01)
(52) U.S. Cl. .......................... 435/377; 435/325; 435/366
(58) Field of Classification Search .................. None
See application file for complete search history.

(56) References Cited

U.S. PATENT DOCUMENTS

| | | | | |
|---|---|---|---|---|
| 4,654,304 A | * | 3/1987 | Seijiro et al. ................... | 435/387 |
| 5,380,660 A | * | 1/1995 | Jefferson et al. .............. | 435/408 |
| 5,968,546 A | * | 10/1999 | Baur et al. ..................... | 424/444 |
| 6,692,961 B1 | * | 2/2004 | Judd et al. ...................... | 435/406 |

OTHER PUBLICATIONS

Liebert et al, Differentiation, 1997, vol. 61, pp. 177-185.*
Scriven et al, The Journal of Urology, 1997, vol. 158, pp. 1147-1152.*
Zhang et al, In Vitro Cell. Dev. Biol.-Animal, 2001, vol. 37, pp. 419-429.*
Freshney, R.I., Culture of Animal Cells: a Manual of Basic Technique. 3rd Ed. Wiley-Liss, New York., 1994, http ://www.hyclone.com/pdf/procedure_passage.pdf , p. 1.*
Reznikoff et al. "Growth and Characterization of Normal Human Urothelium in Vitro", In Vitro, 1983, vol. 19, No. 4, pp. 326-343.*
Cross, William R et al., "The Barrier Function of in Vitro Generated Human Urothelium," Journal of Urology, vol. 167, No. 4 Supplement, Apr. 2002, pp. 32. & Annual Meeting of the American Urology Association Inc.; Orlando Florida, USA; May 25-30, 2002 ISSN: 0022-5347.
Cross William.R. et al., "The Barrier Properties of in Vitro Generated Normal Human Urothelium," Biochemical Society Transcations, vol. 30, No. 1, 2002, p. A44, & 675th Meeting of the Biochemical Society Joint with the Physiological Society; York, England, UK; Dec. 18-19, 2001 ISSN: 0300-5127 abstract.
Truschel, Steven et al., "Primary Uroepithelial Cultures: A Model System to Analyze Umbrella Cell Barrier Function," Journal of Biological Chemistry, vol. 274, No. 21, May 21, 1999, pp. 15020-15029, & ISSN: 0021-9258.
Southgate J. et al.,"Normal Human Urothelial Cells in Vitro: Proliferation and Induction of Stratification," Laboratory Investigation, A Journal of Technical Methods and Pathology, vol. 71, No. 4, Oct. 1994, pp. 583-594 ISSN: 0023-6837.
Southgate, J. et al., "Culture of Human Urothelium," Culture of Epithelial Cells, Second Edition, 2002, pp. 381-399.
Kreft, Mateja et al., "Antigenic and Ultrastructural Markers Associated with Urothelial Cytodifferentiation in Primary Explant Outgrowths of Mouse Bladder," Cell Biology International, vol. 26, No. 1, 2002, pp. 63-74, ISSN: 1065-6995.
Scriven S.D. et al., "Urothelial Cell Transplantation Using Biodegradable Synthetic Scaffolds," Journal of Materials Science: Material in Medicine 2001 Netherlands, vol. 12, No. 10-12, 2001, pp. 991-996 ISSN: 0957-4530.
Sugasi Sita et al., "In Vitro Engineering of Human Stratified Urothelium: Analysis of its Morphology and Function," Journal of Urology, vol. 164, No. 3, Part 2 of 2, Sep. 2000, pp. 951-957 ISSN: 022-5347.
Ludwikowski B. et al., "The Long-Term Culture of Porcine Urothelial Cells and Induction of Urothelial Stratification," BJU International, vol. 84, No. 4, Sep. 1999, pp. 507-514, ISSN: 1464-4096.
Pariente J.L. et al., "Cultured Differentiated Human Urothelial Cells in the Biomaterials Field," Biomaterials, vol. 21, No. 8, Apr. 2000, pp. 835-839 ISSN: 0142-9612.
Deng, Fang-Ming et al., "Uroplakin IIIb, A Urothelial Differentiation Marker, Dimerizes with Uroplakin Ib as an Early Step of Urothelial Plaque Assembly," The Journal of Cell Biology, vol. 159, No. 4, Nov. 11, 2002, pp. 685-694.
Lewis, Simon A., "Everything You Wanted to Know About the Bladder Epithelium But Were Afraid to Ask," Am. J. Physiol Renal Physiol, 278. F867-F874, 2000.
Hutton, K.A.R. et al., "Urothelial Tissue Culture for Bladder Reconstruction: An Experimental Study," The Journal of Urology, vol. 150, Aug. 1993, pp. 721-725.
Schmidt, Wesley et al., "Cultures of Normal Human Urothelial Cells From Ureters of Perfused Cadaver Transplant Kidneys," The Journal of Urology, vol. 132, December, pp. 1262-1264.
Chopra, B. et al.; Trans-Species Comparison of PPAR and RXR Expression by Rat and Human Urothelial Tissues; Toxicol Pathol OnlineFirst; Apr. 25, 2008; vol. XX, No. X, XXXX, Society of Toxicologic Pathology.
Cross, W. R. et al.; A biomimetic tissue from cultured normal human urothelial cells: analysis of physiological function; Am J Physiol Renal Physiol; Mar. 22, 2005pp. F459-F468; vol. 289; the American Physiological Society.

(Continued)

*Primary Examiner* — Laura Schuberg
(74) *Attorney, Agent, or Firm* — Workman Nydegger

(57) ABSTRACT

Urothelium is the specialized endothelium that lines much of the mammalian urinary tract. This invention relates to the field of in vitro urothelial culture. Previous methods produce tissue lacking much of the functionality of native urothelium. In this invention, stratified, differentiated mammalian urothelium is produced by passaging urothelial cells through a nutrient medium containing serum, and redispersed, before going on in a like medium to form said urothelium.

12 Claims, 2 Drawing Sheets

OTHER PUBLICATIONS

Ehmann, U. K. & Terris, M. K.; Long-Term Culture of Porcine Bladder Epithelial Cells, In Vitro Cell. Dev. Biol.—Animal, Mar. 2002, pp. 137-141; vol. 38; Society for in Vitro Biology.

Kurzrock, E. A., Rat Urothelium: Improved Techniques for Serial Cultivation, Expansion, Freezing and Reconstitutuion Onto Acellular Matrix; The Journal of Urology; Jan. 2005, pp. 281-285; vol. 178; American Urological Association, USA.

Turner et al.; Generation of a Functional, Differentiated Porcine Urothelial Tissue in Vitro; Journal, Reconstructive Urology; European Urology; 2008; 1423-1432; 54; Elsevier B.V.

* cited by examiner

BIOMIMETIC UROTHELIUM

FIELD OF THE INVENTION

This invention relates to a method of in vitro cultivation of mammalian urothelium. The invention also relates to material produced by the method described.

REVIEW OF THE ART KNOWN TO THE APPLICANT

The mammalian bladder and associated urinary tract is lined by urothelium, a highly specialised epithelium that provides an effective barrier between the urine and the underlying tissues of the body. With reference to FIG. 1, which shows a schematic diagram of a section through typical, functional urothelium, the urothelium 1 is a stratified epithelium composed of basal 6, intermediate 5 and superficial 4 cells. With the exception of actively transported substances, the urothelium should be impermeable to all substances present in the urine or blood. Movement across the epithelium occurs via two parallel pathways: through the cells (a transcellular pathway) and through the tight junctions 7 and lateral inter-cellular space (a paracellular pathway). Highly-specialised superficial or so-called "umbrella" cells 4 form a tissue-urine interface and provide the permeability barrier through the presence of: a) inter-cellular tight junctions and b) plaques of asymmetric unit membrane (AUM) that cover the apical (i.e. urine-facing) surface. The AUM plaques are unique to the urothelium and are composed of four major urothelium-specific proteins, collectively known as the uroplakins. These proteins have been isolated and cloned. There are two 4 transmembrane domain proteins (4TM proteins), UPIa and UPIb, and also two type 1 proteins, UPII and UPIII. A third type 1 protein has recently been identified. Although the nomenclature is not fully settled, it is likely that the proteins will be referred to as UPII, UPIIIa and UPIIIb. (see Deng F M, Liang F X, Tu L, Resing K A, Hu P, Supino M, Hu C C, Zhou G, Ding M, Kreibich G, Sun T T. "Uroplakin IIIb, a urothelial differentiation marker, dimerizes with uroplakin Ib as an early step of urothelial plaque assembly" J. Cell Biol. 2002 Nov. 25; 159(4):685-94.

A very sensitive method and well-established measure of the ion permeability of epithelium is the transepithelial electrical resistance (TER). In general, leaky epithelia typically have a resistance of less than 500 $\Omega cm^2$, whereas tight epithelia have resistances of greater than 500 $\Omega cm^2$. As a result of its key requirement to protect underlying tissue from urine, urothelium has a characteristically high TER.

Aside from its very low passive permeability to small molecules such as urea, ammonia, water, and protons, and also to large molecules such as dextrans, urothelium also possesses an active transepithelial ion transport system. Of particular importance is the active sodium transport system. With reference to FIG. 1, on the apical (urine facing) surface 2 of the urothelium 1 are located amiloride-sensitive sodium channels 8. On the baso-lateral surface 3 of the urothelium 1 is located a $Na^+$—$K^+$ ATPase antiport system 9, that may be inhibited by the action of ouabain. The presence and correct spatial location of these ion transport systems can be determined through electro-physiological studies by measuring the amiloride-sensitive and ouabain-sensitive potential difference across isolated urothelium.

Thus, the following features are indicative of functional urothelium:

(1) The stratified morphology of basal, intermediate, and "umbrella" cells, (2) The presence of uroplakin protein plaques on the apical surface of the membrane, (3) The presence of tight junctions between the cells of the membrane, (4) The spatially-correct location of amiloride-sensitive sodium channels, and basolateral expression of $Na^+$—$K^+$ ATPase, (5) A high transepithelial resistance, (6) Low passive permeability to other small and large molecular weight species.

A recent review of the state of knowledge of bladder epithelium (urothelium) is provided by Lewis (American Journal of Physiology—Renal Physiology, 2000, 278: F867-F874).

There would be considerable advantage in being able to produce in vitro cultivated urothelium, for a number of reasons. It would provide a model for the study of both normal physiological, and pathophysiological function; it would provide a model for the study of action of pharmaceutical compounds, for example as part of the process of drug discovery (current methods include the use of either undifferentiated or tumour cell culture, neither of which is regarded as a good model for the natural tissue); it would also provide a model for toxicological testing, including but not limited to the assessment of oncogenic potential of substances; it would also provide material for use in reconstructive surgery.

Undifferentiated primary cultures of urothelial cells were first propagated in vitro in the early 1980's, and since then numerous attempts have been made to develop a functional mammalian urothelial cell culture model. However, despite a number of advances, no system has thus far been described in which the in vitro-generated urothelium morphologically and functionally resembles native urothelium, as discussed above.

In 1993 a method was disclosed (K. R. Hutton et al, the Journal of Urology, Volume 150, 71-75, August 1993) for urothelial tissue culture. Urothelium was isolated from clinical tissue samples, by micro-dissection and the use of proteolytic enzymes. The detached urothelium sheets were further treated with collagenase to yield a single cell suspension. The cells could be successfully cultivated on serum-free medium for at least 7 passages. Although confluent sheets of urothelial cells could be produced by this method, no evidence of stratification of the epithelium was observed, and indeed immuno-labelling with differentiation-associated antibody markers demonstrated that although the cultured cells expressed a basal/intermediate cell phenotype, there was no evidence of terminal differentiation.

In a study published in 1994, Southgate et al (Laboratory Investigation, Vol. 71, No 4, Page 583) disclosed the effect of increasing calcium concentration on the stratification of in vitro cultured human urothelial cells. In this study, the tissue samples from renal pelvis, urinary bladder, and ureter were obtained from a total of 62 patients with an age range of 3 months to 23.2 years. Single cell cultures of urothelium were obtained by treatment of tissue with EDTA (ethylenediaminetetraacetic acid) followed by enzymatic digestion. Increasing the extra-cellular calcium concentration in the serum-free growth medium was found to have a marked effect on urothelial cell morphology in all the cell lines examined Increasing the calcium concentration from 0.09 mM to 2.0 mM induced the stratification of the cultured cells, although, despite the multi-layering and evidence of the formation of tight junctions, no AUM was seen in the superficially positioned cells, indicating that late or terminal differentiation had not been obtained. The study did demonstrate, however that donor age is not an important factor for successful urothelial cell culture. Furthermore no discernible differences were observed in the growth properties and phenotype of cultured urothelia initiated from tissue samples from different regions of the urinary tract.

In a study published in 1997, Liebert and her co-workers (Liebert et al, Differentiation, 1997, 61: 177-185) cultured urothelial cells on a serum-free growth medium, and then studied their characteristics after transfer to growth medium supplemented with 2% foetal and 8% newborn calf serum. Although the study appeared to demonstrate a high transepithelial electrical resistance (albeit by the use of the not particularly reliable method of "chopstick" electrodes) no cellular differentiation was reported using any recognised urothelium-specific markers.

In order to compare the relative effectiveness of the method disclosed in Liebert et al, with the present invention, the following study has been undertaken: primary cultures of human urothelium cells were established in serum-free medium as described below. A sample of the cells was plated onto membrane filters, and transferred to cell culture medium containing bovine serum. This is in essence the protocol of Liebert et al. A second sample of the cells was passaged into serum-containing medium according to the preferred embodiment of the current invention described below, before plating onto snapwell membranes, and incubating, again in serum-containing medium as described below. Following seven days growth of the cells the transepithelial electrical resistance of the tissue produced was assessed by use of a modified Ussing chamber and an electric volt-ohm meter. The TER of the tissue cultivated by essentially the protocol of Liebert et al showed a TER of 18.6 $\Omega cm^2$. By contrast, replicate samples of urothelium tissue produced by the method of the current invention showed a mean TER of 3023.4 $\Omega cm^2$. Thus, the former method failed to produce high transepithelial resistance characteristic of functional urothelium.

In 2000 Sugasi and co-workers (The Journal of Urology, Vol. 164, 951-957, September 2000) described the in vitro engineering of human urothelium. Urothelial cells were obtained from tissue samples by separating the urothelium from the underlying stroma, separating the cells by use of collagenase, and culturing the cells in Keratinocyte Serum-Free Medium (KSFM), supplemented with recombinant epidermal growth factor, bovine pituitary extract, cholera toxin and antibiotics. Upon reaching 100% confluence the serum-free medium was enriched with calcium to a final concentration of 1.5 mM to induce stratification. This procedure had already been demonstrated to induce stratification by Southgate et al, 1994, (cited above) but does not induce urothelial differentiation.

SUMMARY OF THE INVENTION

In the broadest definition of the invention, there is provided a method of production of stratified, differentiated mammalian urothelium in which urothelial cells, isolated from the mammalian body, are passaged through a nutrient medium containing the components of serum and redispersed before going on in a like medium to form said urothelium. Preferably, the mammalian urothelium is human urothelium.

Preferably also, the serum is bovine serum, and more preferably the serum is adult bovine serum.

Advantageously, the concentration of the components of serum as a proportion of the final volume of nutrient medium is between about 1% and about 30% related to the concentration of said components in whole serum. More advantageously, the concentration of the components of serum as a proportion of the final volume of nutrient medium is between about 3% and about 10% related to the concentration of said components in whole serum. Most advantageously, the concentration of the components of serum as a proportion of the final volume of nutrient medium is between about 4% and about 6% related to the concentration of said components in whole serum.

Preferably also, the nutrient medium is, or is a derivative of, MCDB-153 medium.

More preferably, the nutrient medium is KSFM (Keratinocyte Serum Free Medium).

Advantageously, the nutrient medium is supplemented by one or more of Epidermal Growth Factor (EGF); Bovine Pituitary Extract (BPE); Cholera Toxin (CT), for reasons described below.

Included within the scope of the invention is a process for the production of stratified, differentiated mammalian urothelium substantially as described herein.

Another aspect of the invention is urothelium produced by the method, as described above.

DESCRIPTION OF THE PREFERRED EMBODIMENT

Figure 1:
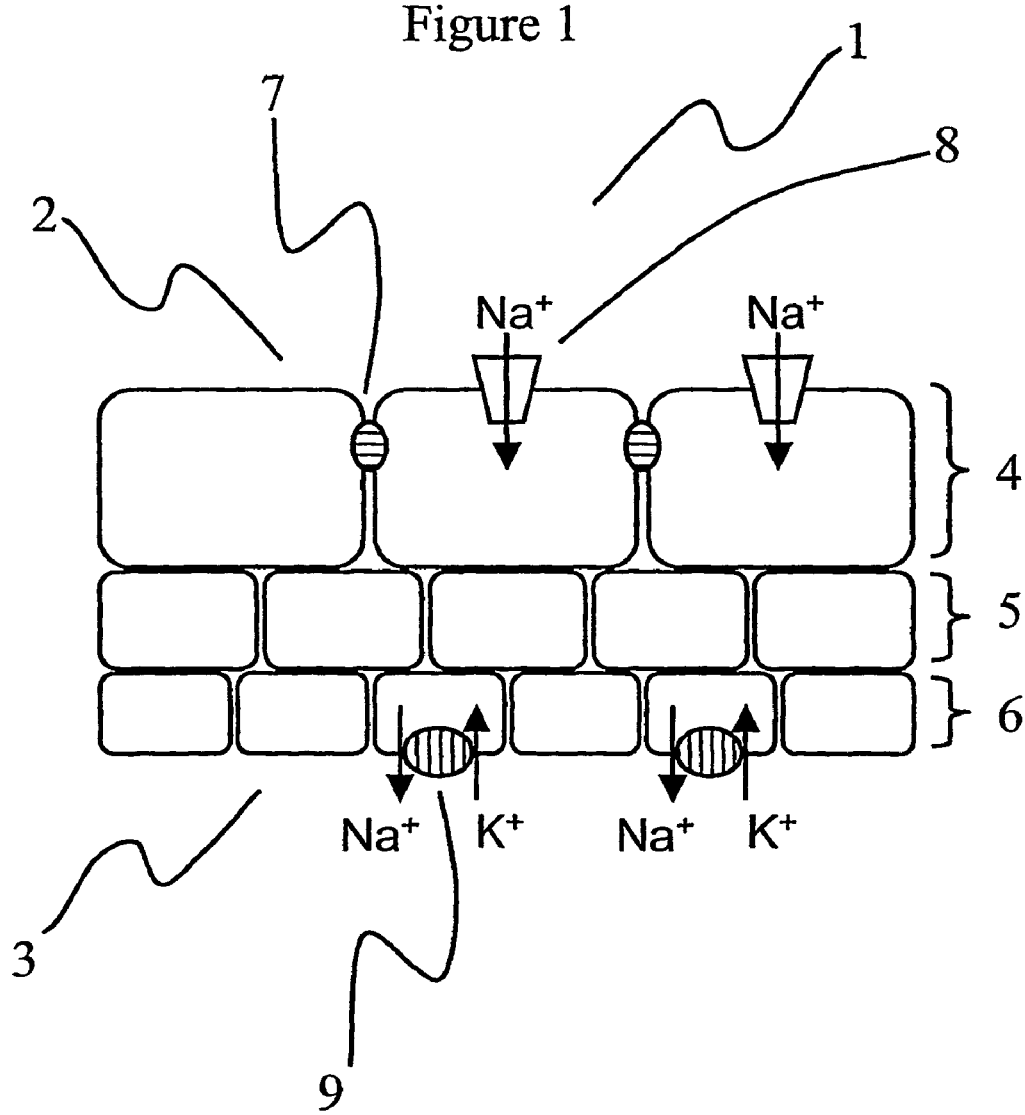
FIG. 1 shows a schematic diagram of a section through typical, functional urothelium, as previously mentioned.

The preferred embodiment of the invention will now be described by means of a description of each of the phases of the method.

Sources of Tissue

Urothelium lines the urinary tract from the renal pelvis through the ureter and bladder to the first part of the urethra. Urothelial cell cultures can be generated readily from each of these regions and no major differences have been found in cell cultures established from different regions of the urinary tract or from adult or paediatric donors. Preferably, tissue for urothelial cell culture can be obtained from biopsies taken under local anaesthetic or from tissue removed at surgery. Diathermy should be avoided in the area round the tissue to be harvested, as this adversely affects the cell viability. Alternatively, urothelial cells may be obtained from samples of urine, using appropriate methods of either cell identification, cell selection or cell sorting, to ensure the cells collected are indeed of urothelial origin. Also, urothelial tissues may be harvested from cadavers, as described by Schmidt and co-workers (Journal of Urology, 1984, 132:1262-1264).

The urothelium is separated from any attached stroma by any of a number of methods recognised by those skilled in the art. Preferably, the specimen of urothelium is trimmed to remove serosa, fat, or other debris, and transferred into a stripping solution comprising HEPES buffer, a protease inhibitor such as aprotinin, EDTA (ethylenediaminetetraaceticacid, disodium salt) and HBSS (Hank's balanced salt solution) without calcium and magnesium. A detailed description of this methodology is described in Southgate J., Masters, J. R. W., and Trejdosiewicz, L. K., "Culture of Human Urothelium", In: Freshney, R. I. and Freshney, M. G., (Eds.) "Culture of Epithelial Cells", 2nd edition, 2002, John Wylie & Sons Inc.

Alternatively, the urothelial cells can be separated from the underlying stroma by mechanical scraping of the urothelial surface of the tissue samples.

Primary Urothelial Cell Culture

If the urothelial cell material has been isolated as urothelial sheets as described in the preceding section, or is in the form of aggregated cells isolated from urine, a culture of dispersed cells may be obtained by any of the methods well known in the art. Collagenase may be used, if required, to release the cells from the underlying tissues.

Suitable medium for the culture and sub-culture of the urothelial cells include KSFM (keratinocyte serum-free medium); MEM (minimal essential medium); and other similar low calcium media suitable for culture of keratinocytes, and preferably based on MCDB-153 medium, and optionally, but preferably containing supplements as described in Southgate et al (Laboratory Investigation, 71(4), 583-594, 1994), drawn from the following list:

(i) Epidermal Growth Factor (EGF), preferably human recombinant EGF, at a final concentration of about 0.05 to about 0.5 ng/ml. Urothelial cells express genes for EGF receptors, and EGF has been demonstrated to be a growth factor for urothelial cells, and gives longevity to the cell lines.
(ii) Bovine Pituitary Extract (BPE), at a concentration of about 10 to about 50 µg/ml, which is required for the long-term survival of urothelial cell lines.
(iii) Cholera Toxin (CT), at a concentration of about 10 to about 75, and preferably about 30 ng/ml, which improves the plating efficiency of the primary culture.

Suitable antibiotics to control the growth of contaminating organisms may also be added, although such additions may mask the presence of such contaminating organisms without eliminating them, and so their absence is to be preferred.

The urothelial cells may then be grown in a substantially conventional way, and maintained by serial sub-culture, or passage, most preferably before the cells reach 100% confluence. The primary, and substantially undifferentiated, cell culture thus attained may be maintained for extended periods of time by such sequential sub-culture, or passage.

Induction of Stratification and Terminal Differentiation

In order to induce stratification and differentiation of the cell culture, cells from the primary cell culture described above are, according to the method of this invention, passaged through a differentiation medium. The differentiation medium of this invention will comprise in addition to a standard cell culture medium (such as KSFM, MEM and other similar low calcium media suitable for culture of keratinocytes, and preferably based on MCDB-153 medium) the components of serum, preferably bovine serum, more preferably foetal bovine serum, and most preferably adult bovine serum, in a concentration from about 1% to about 30%, preferably about 5%, by volume, said percentages being based on the total volume of the differentiation medium, and related to the concentration of said serum components in whole serum. Although said serum is most preferably incorporated as a component of said differentiation medium prior to introducing the urothelial cells into the differentiation medium, it may optionally be added to the medium at any time up to about 5 hours after introduction of the urothelial cells into the medium.

Serum, especially bovine serum is used to supplement a standard cell culture medium as described above. Whilst foetal, newborn or adult bovine serum produce the required differentiation, adult serum is particularly effective at inducing differentiation. This is quite surprising. Having been taught to not only use serum in a growth medium, but also to passage cells through a serum-containing differentiation medium, the skilled addressee would be most likely to use foetal serum as this is often thought to contain developmental factors that may aid differentiation.

In addition, said differentiation medium may optionally, but preferably contain supplements as described in Southgate et al (Laboratory Investigation, 71(4), 583-594, 1994), drawn from the following list:

(i) Epidermal Growth Factor (EGF), preferably human recombinant EGF, at a final concentration of about 0.05 to about 0.5 ng/ml. Urothelial cells express genes for EGF receptors, and EGF has been demonstrated to be a growth factor for urothelial cells, and gives longevity to the cell lines.
(ii) Bovine Pituitary Extract (BPE), at a concentration of about 10 to about 50 µg/ml, which is required for the long-term survival of urothelial cell lines.
(iii) Cholera Toxin (CT), at a concentration of about 10 to about 75, and preferably about 30 ng/ml, which improves the plating efficiency of the primary culture.

Suitable antibiotics to control the growth of contaminating organisms may also be added, although such additions may mask the presence of such contaminating organisms without eliminating them, and so their absence is to be preferred.

In order to induce stratification and differentiation by the method of this invention, cells from the primary cell culture described above are disaggregated by means well known in the art, for example by use of trypsin and EDTA. For an example of a suitable protocol for disaggregation, see Southgate et al ("Culture of Human Urothelium", as above). The disaggregated cells are transferred to the said differentiation medium, and incubated in a substantially conventional manner until they approach confluency. Following this passage through said serum-containing differentiation medium, the cells are once more disaggregated in a substantially conventional manner, and again transferred to fresh serum-containing differentiation medium. This medium, seeded with the urothelial cells, may then be incubated in any substantially conventional cell culture apparatus, or alternatively plated onto any suitable support device, such as polycarbonate Snapwell filters. Following incubation for between about 1 hour and about 48 hours, preferably about 24 hours, the calcium concentration in the growth medium is increased to between about 0.2 mM, and about 5 mM, preferably about 2 mM. Over the following few days, typically after 7 days, the cells will grow to form a substantially functional and terminally-differentiated urothelium. At this stage, the urothelium may be characterised according to morphological and functional criteria as described below.

EXAMPLE

Production and Characterisation of Human Urothelium According to the Method of the Invention Production of Human Urothelium. In vitro, primary, undifferentiated cultures of human urothelial cells were established and propagated through serial passage in serum-free, low calcium KSFM (Gibco BRL, Paisley, UK) culture medium, as described by Southgate et al ("Culture of Epithelial Cells", cited above) using donor tissue from a number of human sources. After sufficient cells were generated (after two to four passages), the cells were harvested and seeded into KSFM medium supplemented with 5% by volume foetal bovine serum (FBS). At confluency, the urothelial cells were harvested, and seeded onto Snapwell filters, and maintained in KSFM medium, supplemented with 5% FBS. After 24 hours, the calcium concentration of the medium was increased from 0.09 mM to 2 mM. The phenotype and various functional properties of the urothelial cell cultures were assessed at seven days subsequent to seeding onto the filters. The results of these characterisations are described below.

Phenotypic Characterisation. Microscopic examination of the cultivated urothelium revealed the stratified, and terminally differentiated nature of the urothelium produced by the method of this invention. Particular features clearly evident to a person skilled in the art of mammalian histology included the presence of stratified layers of basal, intermediate and umbrella cells, and the presence of tight junctions between the urothelial cells. The use of indirect immunofluorescence analysis further confirmed the formation of intercellular tight junctions indicated by the presence of the tight junction protein occludin.

Transepithelial Electrical Resistance (TER). The transurothelial electrical resistance of the in vitro urothelium produced by the method of the invention was measured using a modified Ussing chamber and an electronic volt-ohm meter. The TER of in vitro cultivated urothelium produced by the method of this invention was measured on samples produced on seven separate occasions. The mean TER was found to be $3023.4 \pm 564.4$ $\Omega cm^2$. By contrast, confluent layers of urothelial cells cultured on KSFM medium alone were found to have a TER of $12.7 \pm 1.9$ $\Omega cm^2$.

Transurothelial Permeability. The diffusive water and urea permeabilities of the urothelial sheet produced by the method of this invention were determined using a radio isotope tracer technique. The mean permeability to urea and water respectively were $10.1 \times 10^{-5}$ centimeters per second and $4.5 \times 10^{-4}$ centimeters per second These measured permeabilities were statistically significantly smaller than those obtained for urothelial sheet cultured on KSFM medium alone, these being $12.7 \times 10^{-5}$ centimeters per second and $5.2 \times 10^{-4}$ centimeters per second for urea and water respectively.

Figure 2:
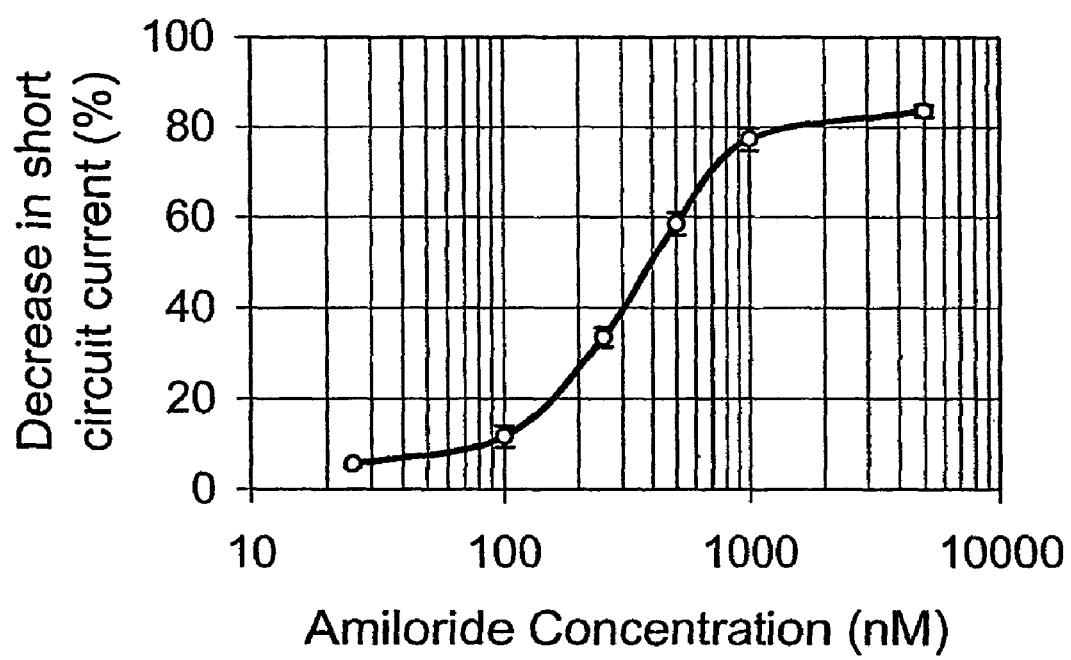
FIG. 2 is a graph showing the dose-responsive decrease in short circuit current across urothelium on the addition of amiloride to the apical surface.

Polarised Sodium Ion Channel Distribution. In order to determine the presence and correct spatial location of sodium ion channels, short circuit current and transepithelial potential difference were measured under voltage and current clamped conditions respectively. The exposure of the apical surface of the urothelial tissue to amiloride reduced both the voltage and the current in a dose-dependent manner. FIG. 2 shows the dose-dependent decrease in short circuit current as a function of the amiloride concentration at the apical surface. Exposure of the basal surface of the urothelial membrane to amiloride did not affect either the voltage or the current. These results indicate that the amiloride-sensitive sodium channels were located on, and restricted to the apical membrane, as required in functional urothelium. Exposure of the apical surface of the in vitro cultivated urothelium to ouabain had only a minor effect on the measured voltage and current. By contrast, when the basal surface of the membrane was exposed to ouabain, there was a marked reduction of both voltage and current, indicating the correct baso-lateral positioning of the $Na^+$—$K^+$ ATPase.

Expression of AUM Protein. The expression of the uroplakin UPIa, UPIb, UPII, and UPIII genes in the in vitro cultivated urothelium of the present invention was confirmed at the mRNA level by the use of reverse transcriptase PCR with appropriate primers.

The above characterisation of the phenotypic and functional characteristics of urothelial tissue produced by the method of the current invention demonstrates the urothelium so produced exhibits more of the functional characteristics of native urothelium than is demonstrated in any of the methods known in the prior art. The observation that researchers skilled in the art of both mammalian cell culture and, more specifically, urothelial cell culture, have attempted to produce functional in vitro urothelium for almost 20 years without success, is testament to the inventiveness of the invention described here.

The invention so described is envisaged to be applicable to the production of mammalian, including human, urothelium.

Various publications are cited herein, the disclosure of which are incorporated by reference in their entireties.

The invention claimed is:

1. A method of production of stratified, terminally-differentiated human urothelium, the method comprising:
    propagation by serial culture of human urothelial cells in a serum-free nutrient medium;
    replacing the serum-free nutrient medium with a first differentiation cell culture medium that includes whole serum;
    maintaining the urothelial cells in the first differentiation culture medium to form a cell culture having at least partially confluent, non terminally-differentiated urothelial cells;
    disaggregating and dispersing said non terminally-differentiated urothelial cells into a fresh second differentiation cell culture medium that includes whole serum; and
    culturing the urothelial cells in the second differentiation culture medium so as to form stratified, terminally-differentiated human urothelium.

2. A method as in claim 1, wherein the non terminally-differentiated urothelial cells approach confluency before the disaggregating and dispersing step.

3. A method as in claim 1, wherein the serum is at a concentration between about 1% and about 30% of the medium.

4. A method as in claim 1, wherein the serum is at a concentration between about 4% and about 6% of the medium.

5. A method as in claim 1, wherein the first differentiation and/or second differentiation cell culture medium includes one of MCDB-153 medium, KSFM (Keratinocyte Serum Free Medium), or a medium derived thereof.

6. A method as in claim 1, wherein first differentiation and/or second differentiation cell culture medium is supplemented by at least one of Epidermal Growth Factor (EGF), Bovine Pituitary Extract (BPE), or Cholera Toxin (CT).

7. A method as in claim 1, wherein the culturing includes increasing the calcium concentration in the second differentiation cell culture medium.

8. The method of claim 1 in which the serum is bovine serum.

9. The method of claim 1 in which the serum is adult or fetal bovine serum.

10. A method as in claim 1, wherein the serum is at a concentration between about 3% and about 10% of the medium.

11. A method of production of stratified, terminally-differentiated human urothelium, the method comprising:
    propagation by serial culture of human urothelial cells in a serum-free nutrient medium;
    replacement of the serum-free nutrient medium with a first differentiation cell culture medium that includes at least 5% whole serum;
    maintaining the urothelial cells in the first differentiation cell culture medium to form a cell culture having at least partially confluent, non terminally-differentiated urothelial cells;

disaggregating and dispersing said non terminally-differentiated urothelial cells into a fresh second differentiation cell culture medium that includes at least 5% whole serum; and culturing the urothelial cells and increasing the calcium concentration of the second differentiation culture medium so as to form stratified, terminally-differentiated human urothelium.

12. A method as in claim 11, further comprising determining the urothelial cells cultured in the second differentiation culture medium to have stratified layers of terminally-differentiated human urothelium.

* * * * *